(12) United States Patent
Meyer et al.

(10) Patent No.: US 7,972,057 B2
(45) Date of Patent: Jul. 5, 2011

(54) DEVICE FOR PRODUCING A MULTI-COMPONENT COMPOUND

(75) Inventors: Sven Meyer, Apensen (DE); Matthias Weihrauch, Klein Nordende (DE); Jürgen Wallbott, Lahnau (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 54 days.

(21) Appl. No.: 12/310,267

(22) PCT Filed: Jul. 18, 2007

(86) PCT No.: PCT/EP2007/006395
§ 371 (c)(1),
(2), (4) Date: Oct. 1, 2009

(87) PCT Pub. No.: WO2008/019745
PCT Pub. Date: Feb. 21, 2008

(65) Prior Publication Data
US 2010/0091607 A1    Apr. 15, 2010

(30) Foreign Application Priority Data

Aug. 18, 2006  (DE) .......................... 10 2006 038 897

(51) Int. Cl.
*B67D 7/74* (2010.01)
(52) U.S. Cl. ..................... 366/172.1; 222/325
(58) Field of Classification Search ............... 366/171.1, 366/172.1–173.2, 176.1, 181.5, 189; 222/145.5, 222/145.6, 325–327
See application file for complete search history.

(56) References Cited

U.S. PATENT DOCUMENTS

| 3,570,719 | A | * | 3/1971 | Schiff | 222/137 |
|---|---|---|---|---|---|
| 3,767,085 | A | * | 10/1973 | Cannon et al. | 222/82 |
| 4,986,443 | A | * | 1/1991 | Saur et al. | 222/1 |
| 5,286,105 | A | * | 2/1994 | Herold et al. | 366/162.3 |
| 6,129,244 | A | * | 10/2000 | Horth | 222/94 |
| 6,315,164 | B1 | * | 11/2001 | Muhlbauer et al. | 222/63 |
| 6,394,643 | B1 | * | 5/2002 | Bublewitz et al. | 366/172.1 |
| 6,457,609 | B1 | * | 10/2002 | Keller | 222/137 |

(Continued)

FOREIGN PATENT DOCUMENTS

DE          3233366 A1 *  9/1983

(Continued)

*Primary Examiner* — Charles E Cooley
(74) *Attorney, Agent, or Firm* — Alix, Yale & Ristas, LLP

(57) ABSTRACT

A device for producing a multi-component compound, in particular for dental purposes, by mixing its components after they have been pressed out of cartridges which open into a dynamic mixer and are arranged exchangeably in the device, with a first motor for advancing all of the pistons assigned to the cartridges, and with a second motor for rotary driving of mixing elements in the mixer via a shaft, which is held in engagement with the mixer by spring pretensioning and can be pulled back from the mixer counter to the spring pretensioning, is characterized in that the shaft is provided with a radially extending projection which, by the spring pretensioning, is pressed onto a ramp-like upwardly sloping cam surface, which is provided on its foot with an abutment surface, of a toothed wheel, which is provided with saw-like teeth and is coaxial to the shaft, which toothed wheel, in a first angle direction in which the cam surface slopes upwards, is prevented from rotating by a catch and, in the second angle position opposite thereto, is rotatable, the mixer drive shaft being pulled back during rotation in the first direction of rotation.

8 Claims, 3 Drawing Sheets

U.S. PATENT DOCUMENTS

| | | |
|---|---|---|
| 6,523,992 B1 * | 2/2003 | Bublewitz et al. .......... 366/172.1 |
| 6,631,829 B1 * | 10/2003 | Wagner et al. ................... 222/23 |
| 6,837,612 B2 * | 1/2005 | Bublewitz et al. .......... 366/172.1 |
| 6,854,621 B2 * | 2/2005 | Keller ........................... 222/137 |
| 6,932,237 B2 * | 8/2005 | Heymann et al. ................. 222/1 |
| 2002/0190082 A1 * | 12/2002 | Keller ........................... 222/129 |
| 2003/0022128 A1 * | 1/2003 | Heymann et al. ............... 433/89 |
| 2003/0123323 A1 * | 7/2003 | Bublewitz et al. .......... 366/172.1 |
| 2006/0071023 A1 * | 4/2006 | Lein et al. ..................... 222/135 |
| 2010/0091607 A1 * | 4/2010 | Meyer et al. ............... 366/151.2 |
| 2010/0252574 A1 * | 10/2010 | Busin ........................... 222/137 |

FOREIGN PATENT DOCUMENTS

| | | | |
|---|---|---|---|
| DE | 3237353 A1 | * | 4/1984 |
| DE | 3303667 A1 | * | 8/1984 |
| DE | 37 38 960 A1 | | 5/1989 |
| EP | 1 279 379 A | | 1/2003 |
| WO | WO 8302712 A1 | * | 8/1983 |
| WO | 2007/041878 A1 | * | 4/2007 |

* cited by examiner

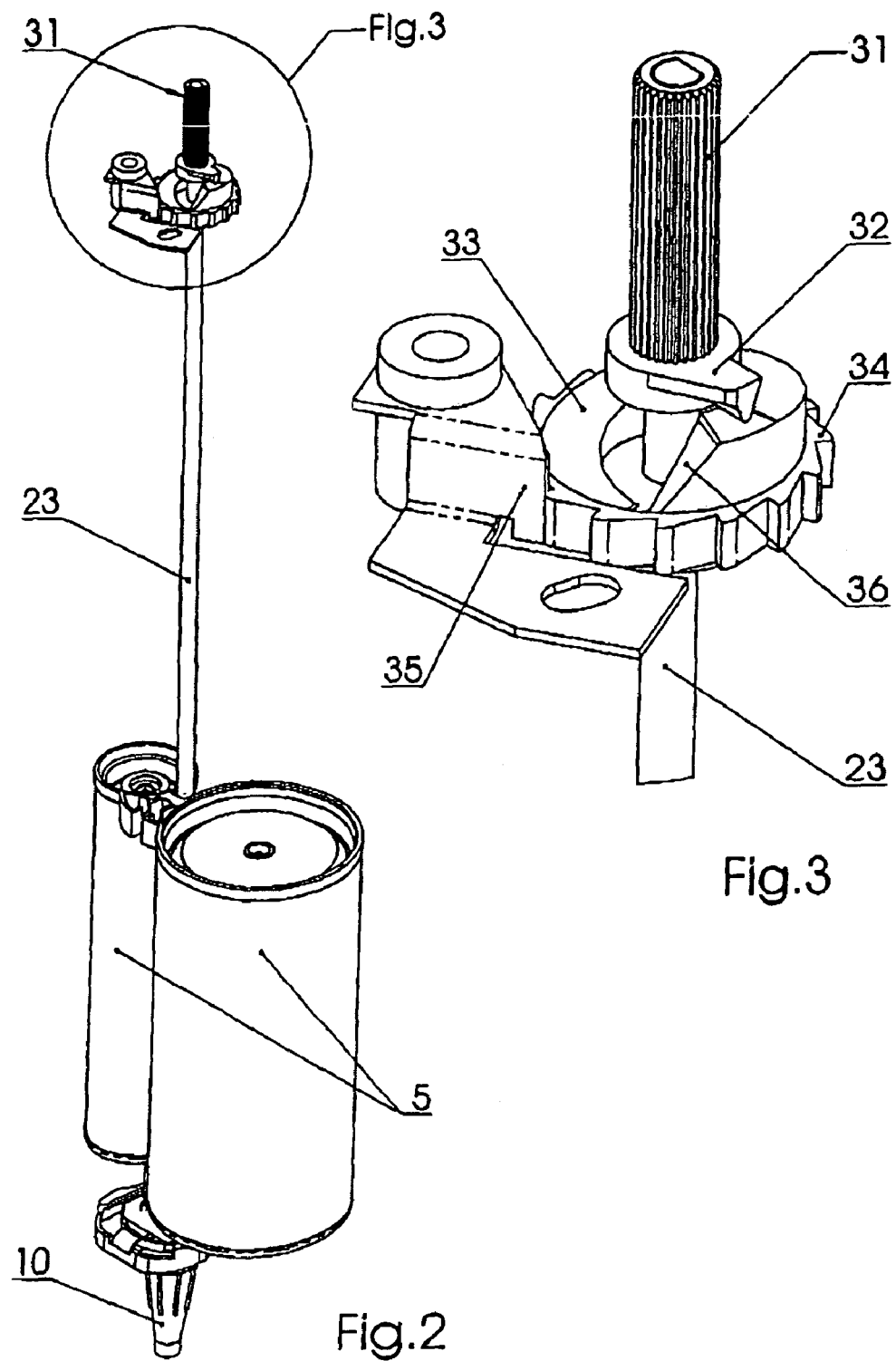

DEVICE FOR PRODUCING A MULTI-COMPONENT COMPOUND

BACKGROUND

The invention relates to a device for producing a multi-component compound, in particular for dental purposes, by mixing its components after they have been pressed out of cartridges which open into a dynamic mixer and are arranged exchangeably in the device, with a first electric motor for advancing all of the pistons assigned to the cartridges, and with a second electric motor for rotary driving of mixing elements in the mixer via a shaft, which is held in engagement with the mixer by spring pretensioning and can be pulled back from the mixer counter to the spring pretensioning.

Multi-component compounds can be dispensed and mixed using a known device of this type (EP 1 279 379 B1). The mixer of said device has to be replaced every so often. This is firstly necessary for hygiene reasons, if the mixed compound remains for too long in the mixer. It is particularly necessary, however, when the mixed compound hardens, since the mixer then becomes unusable after a certain time. In the known device, it is necessary first to pull the pistons back fully for this purpose. At the end of this movement, the shaft driving the mixer is then pulled back and thereby detached from the mixer, which could be done by a cross bracket, for example, that connects the two pistons. The mixer can then be pulled out sideways and replaced by a new one. When the pistons are again moved in order to press the multi-component compounds out, the spring force presses the shaft back into engagement with the mixer.

The disadvantage of this device is that the pistons first have to be fully retracted if the mixer is to be replaced. This does not pose any problems if the cartridges have been completely emptied. In many cases, however, it is desired for the same filling of the cartridges to be partially pressed out a number of times in succession, in which case the mixer has to be replaced if, in the interim, too much time has elapsed between the individual pressing-out operations and the components have therefore at least partially hardened in the mixer. It is in this case disadvantageous if the pistons each have to be fully retracted first of all. This entails a considerable loss of time, particularly in view of the fact that, although the pistons can be retracted quickly, they then have to be brought back very slowly toward the material still located in the cartridges in order to carefully make contact with the material still present therein. The retraction movement could also have the undesired effect of allowing air into the cartridges.

SUMMARY

A device of the type mentioned at the outset is provided, in which the mixer can be exchanged without the pistons being pulled back completely.

A shaft is provided with a radially extending projection which, by means of the spring pretensioning, is pressed onto a ramp-like upwardly sloping cam surface, which is provided on its foot with an abutment surface, of a toothed wheel which is provided with saw-like teeth and is coaxial to the shaft, which toothed wheel, in a first angle direction in which the cam surface slopes upward, is prevented from rotating by a catch and, in the second angle direction opposite thereto, is rotatable.

In a pressing-out mode, the shaft is turned in the second direction of rotation. The projection on the shaft bears at the base of the cam surface on the abutment surface and turns the toothed wheel. If the projection was located on the ramp at the start, it is guided to the abutment by the rotation movement, since the toothed wheel is not freely rotatable, and instead a sufficient resistance force is also generated by the catch in the permitted direction of rotation. However, this is overcome when the projection bears on the abutment surface and in this way turns the toothed wheel. The shaft is then in engagement with the mixer.

If the mixer is to be replaced, the shaft is turned in the first angle direction through a predetermined angle. The toothed wheel is not able to turn too, since it is prevented from doing so by the catch. The projection then travels up the ramp and thus also pulls the shaft upward in the axial direction, such that the shaft is disengaged from the mixer, which can then be replaced.

After a new mixer has been fitted and the mixer is to be operated, turning again takes place in the second direction of rotation. Because of the spring pretensioning, the projection travels down the ramp until it hits the abutment. The shaft engages in the corresponding coupling element of the mixer, such that the latter can be turned.

After a new mixer has been fitted, it is also possible to turn the projection further in the first direction of rotation, beyond the upwardly sloping cam surface, until it bears on the abutment under the action of the spring pretensioning.

The ramp advantageously extends over an angle range of more than 270°. This avoids the need for an especially steep ramp, which would require higher torques for moving the projection up along the ramp.

The ramp, at its upper end, advantageously has an abutment for the projection of the shaft. When the projection reaches this abutment, it cannot be moved any further since the toothed wheel cannot turn in this direction. The resulting higher drive current of the motor can be detected, such that the motor can be switched off.

In another embodiment, or in addition to this, the rotation in the first angle direction is ended by electronic control means after rotation has taken place about a predetermined angle.

When the word "up" is used in the preceding text, this signifies that the axes of the cartridges are oriented substantially vertically, in which case the mixer is then located below, or at least are arranged at such an incline that the mixer is located substantially lower than the main part of the cartridges.

BRIEF DESCRIPTION OF THE DRAWINGS

An advantageous embodiment is described below with reference to the attached drawings, in which:

FIG. 2 shows elements for driving a mixer;

FIG. 3 shows a detailed view of the part circled in FIG. 2;

DETAILED DESCRIPTION

Figure 1:
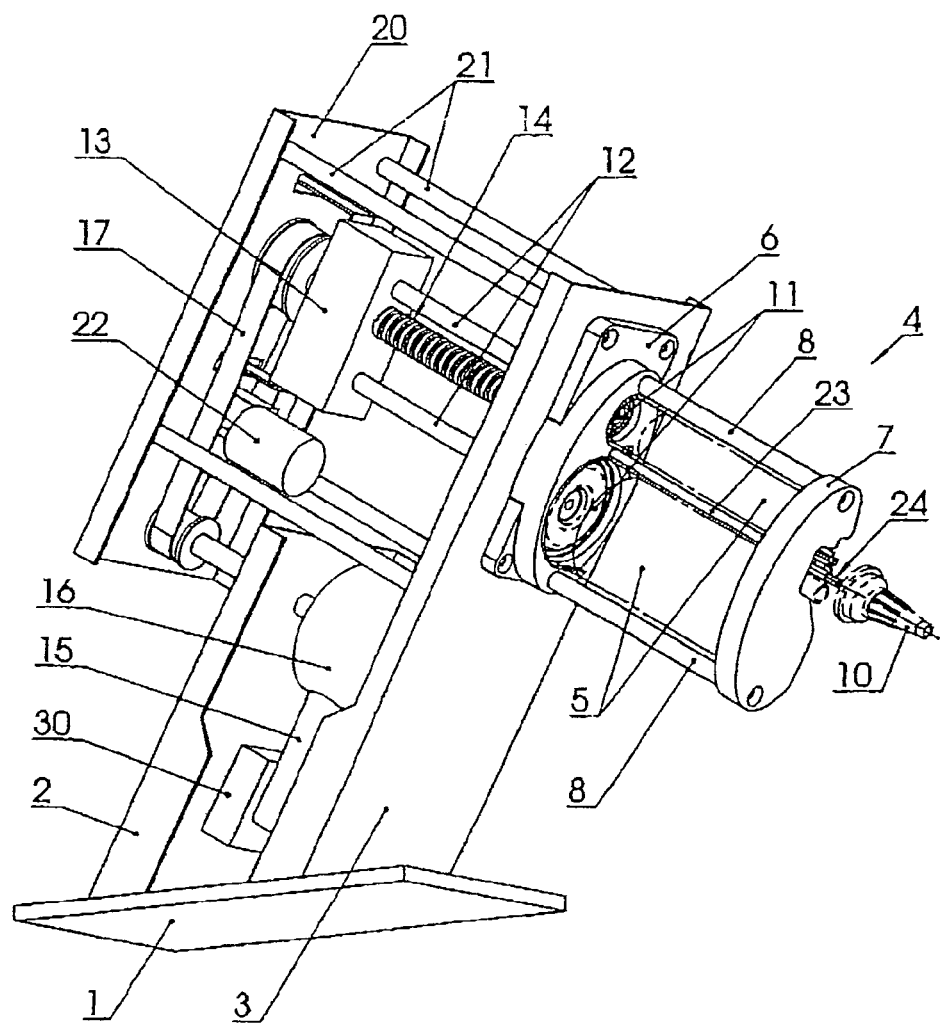
FIG. 1 shows a perspective view of a device according to the prior art.

A known device (EP 1 279 379 A1) in which the invention can be applied will first be described with reference to FIG. 1.

Rising from a base part 1, there are support plates 2, 3. A holder 4 is provided on the latter for cartridges 5, indicated by dot-and-dash lines. In this context it is of no importance whether the cartridges, which are preferably of cylindrical design, are filled directly with the components or receive an optionally exchangeable tubular bag containing the component.

The holder 4 comprises a rear holding plate 6 and a front holding plate 7 which are held together by anchors 8. The cartridges 5 can be fitted between these. Further holding means (not shown) can be provided for the lateral positioning of the cartridges 5.

On the front holding plate 7 there is a means (not shown) for arranging a mixer nozzle 10, indicated by dot-and-dash lines. The mixer nozzle is advantageously pushed in sideways perpendicular to its longitudinal extent, since in this way it can very easily withstand the material pressure of the components as they are pressed out and it is not forced out of its holder by the material. The mixer nozzle 10 has, at its end facing the holding plate 7, two inlet openings which communicate in a known manner directly or indirectly with the outlet openings of the cartridges 5. The feature whereby the cartridges are arranged alongside each other is intended only to signify that they are arranged such that they can be operated simultaneously and synchronously. A positional restriction going beyond this, for example restriction to a parallel arrangement, is not thereby intended, although this is obviously advantageous.

The cartridges 5 contain pistons. These can optionally be omitted if the cartridges contain foil bags. The stamps then take the place of the pistons mentioned in the claim. For advancing the pistons or the rear face of the bags, the device has stamps 11 which, in the drawing, are shown in the state in which they are pulled back into the rear holding plate 6 for the purpose of changing the cartridges. They are arranged at the front end of stamp rods 12, whose rear ends are secured rigidly in a cross bracket 13 which, by means of a threaded spindle 14, can be advanced in the direction toward the mixer nozzle or pulled back in the opposite direction. The stamps 11 can optionally be changed if cartridges of different diameter are to be used. The distance between them can also be varied. When the cartridges 5 are inserted in the device, the stamps 11 are advanced by advancing the cross bracket 13 until they reach the pistons in the cartridges 5. This advance movement can be triggered automatically by the insertion of the cartridges or can be triggered manually by switching on the device.

For the advance and return drive of the threaded spindle 14, a motor 15 with gear 16 is provided, the drive movement of which is transmitted to the threaded spindle 14 via a belt transmission 17. For mounting the threaded spindle 14 and the annular disks belonging to the belt transmission 17, means (not shown) are provided which are arranged on the plate 3 and on a further frame plate 20 which is connected rigidly to the plate 3 via columns 21.

A further motor 22 is arranged on the plate 20 and is connected (in a manner not shown) on the drive side to a mixer drive shaft 23 which lies between the plates 3 and 20 coaxially within the threaded spindle 14, is guided between the cartridges 5 from the rear holding plate 6 to the front holding plate 7, and is mounted in the latter. The mixer drive shaft 23 can be driven by means of belts, for example. It protrudes from the front holding plate 7 in the form of a nose 24 which, for the purpose of rotational connection to the mixer shaft (not shown), has a polygonal design (not shown) for example.

The shaft nose 24 can be pushed back counter to a spring force until it no longer protrudes from the front holding plate 7. Provision can also be made that when the stamps 11 are completely pulled back for the purpose of cartridge exchange, it is likewise pulled back into the front holding plate 7 in order to facilitate the attachment of a new mixer nozzle 10.

An electronic unit 30 is provided, as is indicated schematically at 30. This controls the movement of the pistons. Provision can be made that when the stamps 11 are completely pulled back for the purpose of cartridge exchange, the shaft nose 24 is likewise pulled back into the front holding plate 7 in order to permit or at least facilitate the attachment of a new mixer nozzle 10.

The disadvantage of the stamps 11 having to be fully pulled back before the shaft nose 24 is likewise pulled back and the mixer nozzle 10 can be replaced is now avoided in the device of FIGS. 2 and 3 which show only some of the parts; the other parts correspond to the prior art. In particular, FIG. 2 does not show any of the parts between the support plates 2 and 3; these parts must be imagined as being arranged in the free lengthwise area of the mixer drive shaft 23 in FIG. 2.

The mixer drive shaft is driven by the motor 22 via a toothed wheel 31 which engages with a corresponding driving toothed wheel and is elongate so as to ensure the driving action even upon displacement of the mixer drive shaft 23 in the axial direction. As can be seen in FIG. 2, and in detail in FIG. 3, which shows the circled area from FIG. 2 on an enlarged scale, the mixer drive shaft 23 has a projection 32 which is arranged on an annular element and which can move on an upwardly sloping cam surface 33 of a toothed wheel 34, which is provided with saw-like teeth. A catch 35 ensures that the toothed wheel 34, in the view shown in FIG. 3, can turn only counterclockwise. In the position shown in FIG. 3, the projection 32 is located on the upper end of the cam surface 33. The mixer drive shaft 23 is here drawn upward and away from the mixer nozzle 10 counter to the force of a spring (not shown), such that it is no longer in engagement with the mixer nozzle 10. The mixer nozzle can therefore be removed. After a new mixer nozzle 10 is fitted and the operation of pressing out begins again, the mixer drive shaft 23 is turned in the counterclockwise direction by the motor 22. The friction provided by the catch 35 is sufficient to hold the toothed wheel 34 securely in place, such that the projection 32 can travel down the ramp 33 until it hits an abutment surface 36. The mixer drive shaft 23 is moved downward in the axial direction and into engagement with the mixer nozzle 10. The turning has the effect that the shaft nose 24, which is in correct engagement with the recess 25 corresponding to the shaft nose 24, and the mixing elements are caused to rotate. The toothed wheel 34 also turns with them but at this moment has no further function.

If the mixer nozzle 10 is now to be replaced, the motor and thus the mixer shaft 23 are moved through approximately 270° in the opposite direction, i.e. in the clockwise direction. The toothed wheel 34 is not able to turn with them, because of the action of the catch 35. The projection 32 travels up the ramp 33 and in doing so pulls the mixer shaft 23 back, such that the mixer nozzle can be replaced.

Figure 4:
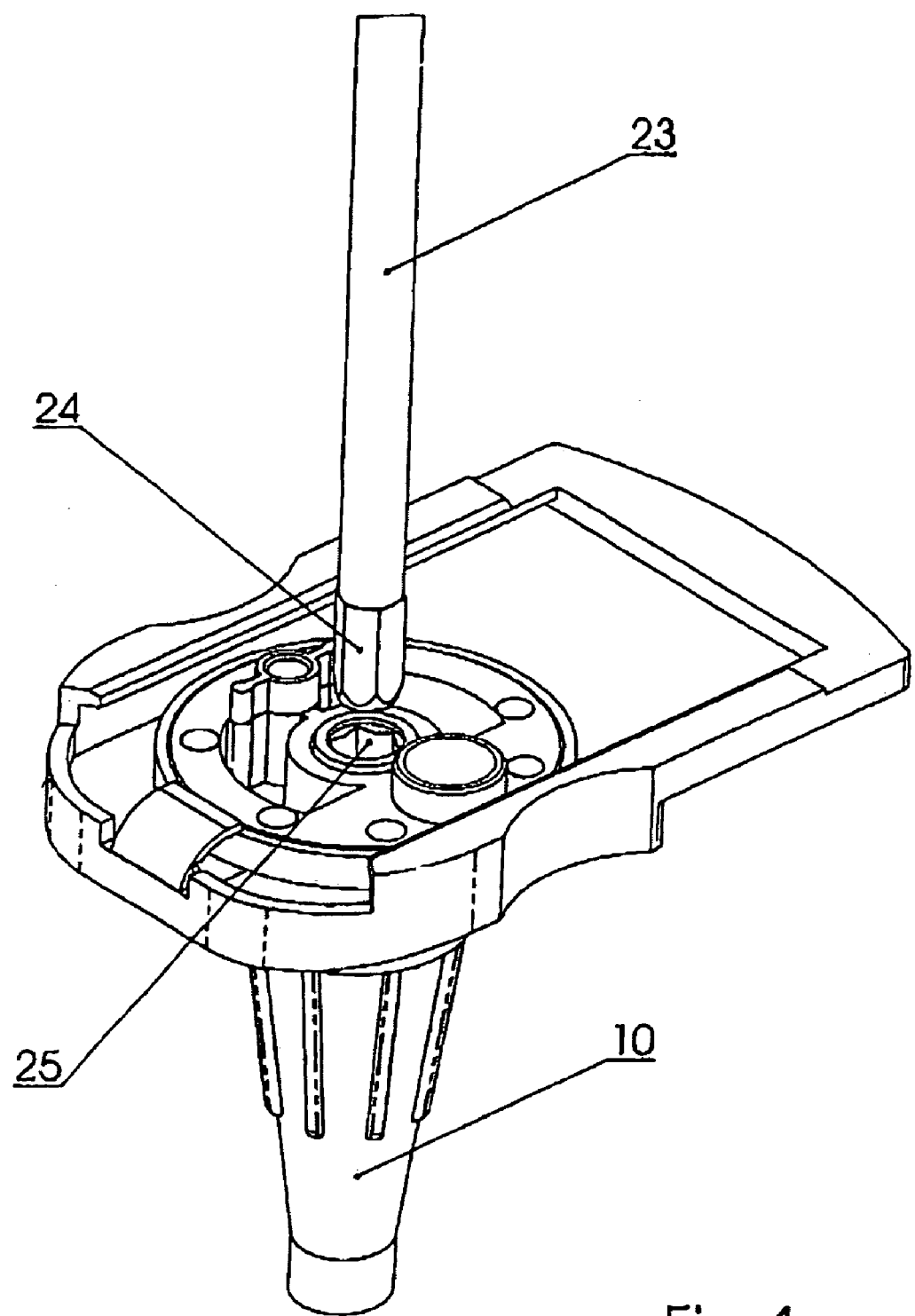
FIG. 4 shows a view of the mixer nozzle and of the mixer drive shaft.

FIG. 4 shows the mixer nozzle 10 in detail and on an enlarged scale, from which mixer nozzle 10 the shaft nose 24 of the mixer drive shaft 23 has been pulled out. The shaft nose 24 has a polygonal design in order to drive the mixer nozzle 10.

The invention claimed is:

1. A device for producing a multi-component compound, in particular for dental purposes, by mixing its components after they have been pressed out of cartridges which open into a dynamic mixer and are arranged exchangeably in the device, with a first motor for advancing all of the pistons assigned to the cartridges, and with a second motor for rotary driving of mixing elements in the mixer via a shaft, which is held in engagement with the mixer by spring pretensioning and can be pulled back from the mixer counter to the spring pretensioning, characterized in that the shaft is provided with a radially extending projection which, by means of the spring pretensioning, is pressed onto a ramp-like upwardly sloping cam surface, which is provided on its foot with an abutment surface, of a toothed wheel which is provided with saw-like teeth and is coaxial to the shaft, which toothed wheel, in a first angle direction in which the cam surface slopes upward, is prevented from rotating by a catch and, in the second angle direction opposite thereto, is rotatable, the mixer drive shaft being pulled back during rotation in the first direction of rotation.

2. The device as claimed in claim 1, characterized in that the ramp-like cam surface extends over an angle range of more than 270°.

3. The device as claimed in claim 2, characterized in that the ramp, at its upper end, has an abutment for the projection of the shaft.

4. The device as claimed in claim 3, characterized in that the rotation in the first angle direction is ended by electronic control means after rotation has taken place about a predetermined angle.

5. The device as claimed in claim 2, characterized in that the rotation in the first angle direction is ended by electronic control means after rotation has taken place about a predetermined angle.

6. The device as claimed in claim 1, characterized in that the ramp-like cam surface, at its upper end, has an abutment for the projection of the shaft.

7. The device as claimed in claim 6, characterized in that the rotation in the first angle direction is ended by electronic control means after rotation has taken place about a predetermined angle.

8. The device as claimed in claim 1, characterized in that the rotation in the first angle direction is ended by electronic control means after rotation has taken place about a predetermined angle.

* * * * *